United States Patent [19]

Luly et al.

[11] Patent Number: 4,725,583
[45] Date of Patent: Feb. 16, 1988

[54] FUNCTIONALIZED PEPTIDYLAMINOALCOHOLS

[75] Inventors: Jay R. Luly; Jacob J. Plattner, both of Libertyville, Ill.

[73] Assignee: Abbott Laboratories, North Chicago, Ill.

[21] Appl. No.: 830,615

[22] Filed: Feb. 18, 1986

Related U.S. Application Data

[63] Continuation-in-part of Ser. No. 693,951, Jan. 23, 1985, abandoned.

[51] Int. Cl.$^4$ .................. A61K 37/43; C07K 5/06; C07K 5/08
[52] U.S. Cl. .................. 514/18; 514/19; 530/331; 530/332
[58] Field of Search ............. 530/800, 331, 332; 514/18, 19

[56] References Cited

U.S. PATENT DOCUMENTS 4,474,764 10/1984 Umezawa et al. .................. 530/331
4,548,926 10/1985 Matsueda et al. .................. 530/800

OTHER PUBLICATIONS

Biochem. and Biophys. Res. Commun., 118, No. 3 (1984), 929–933.
Chem. Abstr., vol. 100 (1984), 187896.
Chem. Abstr., vol. 99 (1983), 122938.
Chem. Abstr., vol. 78 (1973), 119129.
Chem. Abstr., vol. 79 (1973), 66807.
Chem. Abstr., vol. 93 (1980), 205010.
Chem. Abstr., vol. 100 (1984), 151619.
Chem. Abstr., vol. 102 (1985), 91909.

*Primary Examiner*—Delbert R. Phillips
*Attorney, Agent, or Firm*—Steven F. Weinstock; Martin L. Katz

[57] ABSTRACT

The invention relates to renin inhibiting compounds of the formula

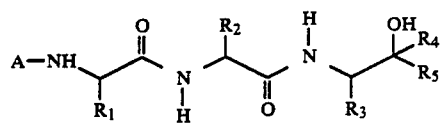

wherein A is an N-protecting group; $R_1$, $R_2$ and $R_3$ are independently selected from loweralkyl or lipophilic or aromatic amino acid side chains; and $R_4$ is —CHO, —CO$_2$H, halomethyl or alkanoyl; and $R_5$ is hydrogen or loweralkyl.

6 Claims, No Drawings

4,725,583

FUNCTIONALIZED PEPTIDYLAMINOALCOHOLS

TECHNICAL FIELD

This is a continuation-in-part of U.S. patent application, Ser. No. 693,951, filed Jan. 23, 1985, now abandoned.

The present invention relates to novel organic compounds which inhibit renin, processes for making such compound, synthetic intermediates employed in these processes and method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotension system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula

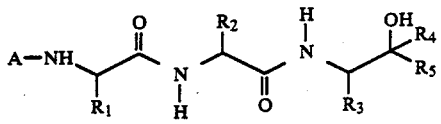

wherein A is an N-protecting group; $R_1$, $R_2$ and $R_3$ are independently selected from loweralkyl or lipophilic or aromatic amino acid side chains; and $R_4$ is $-CHO$, $-CO_2H$, halomethyl or alkanoyl; and $R_5$ is hydrogen or loweralkyl.

The chiral centers of the compounds of the invention may have either the "R" or "S" configuration but preferably have an "S" configuration except where otherwise noted.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), carbobenzyloxycarbonyl or benzoyl groups or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkanoyl" as used herein refers to an carbonyl radical which has appended to it an alkyl radical.

The term "lipophilic or aromatic amino acid side chains" as used herein refers to those amino acid side chains which have an affinity for lipids or have an aromatic ring and include but are not limited to isobutyl, isopropyl, sec-butyl, benzyl, (imidazole-4-yl)methyl, p-hydroxybenzyl, 1- and 2-naphthylmethyl, and cyclohexylmethyl. General reference to amino acid side chains in both the description and claims herein is to be taken as reference to such, whether naturally occurring in proteins or not, and to both D- and L-forms.

The term "halomethyl" as used herein refers to a monohalo-substituted methyl including but not limited to chloromethyl and bromomethyl.

The terms "Ala", "His", "Leu", and "Phe" as used herein refer to alamine, histidine, leucine and phenylalanine, respectively.

The following Examples will serve to further illustrate preparation of the novel compounds of the invention.

EXAMPLE 1

(3RS,4S)-4-t-Butyloxycarbonylamino-3-hydroxy-6-methylhept-1-ene

To a stirred 0° C. solution of Boc-leucinal (3.00 g, 13.9 mmol) in dry tetrahydrofuran (THF) (70 ml) was added vinyl magnesium bromide (35 ml of a 1.0M solution in THF). After 5 hours, the mixture was quenched with 1.0M $NH_4Cl$ (50 ml). Most of the THF was evaporated in vacuo and the residue was extracted with ether several times. The combined extracts were washed (brine), dried ($Na_2SO_4$), filtered, and evaporated to give the desired product as a 3:2 mixture of hydroxy diastereomers in 65% yield.

EXAMPLE 2

Boc-Phe-Ala Amide of (3RS,4S)-4-Amino-3-hydroxy-6-methylhept-1-ene

The resultant product of Example 1 (1.00 g, 4.11 mmol) was treated with 1M HCl/methanol (80 ml) for 15 hours at which time the solvent was evaporated under high vacuum to give 0.74 g of the corresponding amine hydrochloride.

To a stirred $-12°$ C. solution of Boc-Phe-Ala (1.12 g, 3.34 mmol) in anhydrous THF (30 ml) were added N-methylmorpholine (NMM, 338 mg) and isobutylchloroformate (456 mg) sequentially. After 3 minutes, a $-12°$ C. solution of the above amine salt (598 mg) and NMM (338 mg) in THF (10 ml) was added dropwise over 5 minutes. The reaction mixture was warmed at room temperature for 2 hours. Evaporation of the solvent provided a residue which was partitioned between ethyl acetate and aq. $NaHCO_3$. The organic phase was washed with dilute $H_3PO_4$ and then brine. Drying ($Na_2SO_4$) and evaporation provided 1.41 g (92%) of the desired material. Mass spectrum: $M^+ = 461$.

Anal. calcd. for $C_{25}H_{39}N_3O_5 \cdot 1/4H_2O$: C, 64.4; H, 8.5; N, 9.0. Found: C, 64.3; H, 8.3; N, 8.8.

EXAMPLE 3

Boc-Phe-Ala Amide of (3S)-Amino-2-hydroxy-5-methylhexanal

To a rapidly stirred solution of the resultant product of Example 2 (200 mg, 0.433 mmol) in THF (5 ml) was added $OsO_4$ solution (0.136 ml of a 2.5 W/V% solution in t-butanol) followed by $NaIO_4$ (231 mg, 1.08 mmol) in water (5 ml). After 24 hours, the mixture was partitioned between water (10 ml) and ether (10 ml). The aqueous phase was further extracted with ether ($2 \times 10$ ml), and the combined extracts were washed sequentially with 10% $NaHSO_3$ ($3 \times 3$ ml) and brine (5 ml). Drying ($NaSO_4$), filtering, and evaporating gave the desired product (65 mg, 30%) after chromatography. Mass spectrum: $(M+H)^+ = 464$.

Anal. calcd. for $C_{24}H_{37}N_3O_6$: C, 62.2; H, 8.0; N, 9.1. Found: C, 62.3., H, 8.0; N, 9.4.

EXAMPLE 4

Boc-Phe-Ala Amide of (3S)-Amino-2-hydroxy-5-methylhexanoic Acid

A stirred 0° C. solution of the resultant compound of Example 3 (463 mg, 1 mmol) in ethanol (10 ml) was treated sequentially with silver (I) oxide (232 mg, 1 mmol) and 2M NaOH (1.0 ml). The mixture was warmed to room temperature, acidified, filtered, and evaporated to give the desired product.

EXAMPLE 5

(4S)-2,8-Dimethyl-4-[(toluenesulfonyl)amino]-5-nonanone

To a stirred $-78°$ C. solution of Ts-Leu (15 g, 53 mmol) in dry THF (240 ml) was added n-butyl lithium (57.8 ml of a 0.91M solution in hexane) followed 15 minutes later by isopentyl magnesium bromide (185 ml of a 0.8M solution in THF). The mixture was heated at reflux for 3 days, then cooled and poured into 0° C. 1M HCl (500 ml). The layers were separated and the aqueous phase was extracted with ether ($3 \times 150$ ml). The combined organic layers were washed with saturated $NaHCO_3$ ($2 \times 150$ ml) and brine (150 ml). Drying and evaporating provided a residue which was chromatographed on silica gel to give 7.43 g (41%) of the desired product. Mass spectrum: $(M+H)^+ = 340$.

Anal. calcd. for $C_{18}H_{29}NO_3S$: C, 63.7, H, 8.6,. N, 4.1. Found: C, 64.0., H, 8.6; N, 4.1.

EXAMPLE 6

(4S)-2,8-Dimethyl-5-hydroxy-4-[(toluenesulfonyl)amino]-5-vinylnonane

To a stirred 0° C. solution of the resultant compound of Example 5 (79 mg, 0.23 mmol) in dry THF (8 ml) was added vinyl magnesium bromide (1.5 ml of a 1.0M solution in THF) dropwise. The mixture was warmed (room temperature, 10 hours), quenched (8 ml $H_2O + 2$ ml brine), acidified with 0.1M $H_3PO_4$ (pH=7), and extracted with ether ($3 \times 4$ ml). The combined ether phase was washed (4 ml brine), dried ($Na_2SO_4$), filtered, and evaporated to give 81 mg (95%) of the desired product as a 4:1 mixture of diastereomers.

EXAMPLE 7

Boc-Phe-Ala Amide of (4S)-Amino-2,8-dimethyl-5-hydroxy-5-vinylnonane

To a solution of the resultant compound of Example 6 (400 mg, 1.09 mmol) in liquid ammonia (80 ml) was added sodium (150 mg, 6.5 mmol). After 6 hours the ammonia was allowed to slowly evaporate under a stream of nitrogen. Benzene (50 ml) and 1:1, ethanol:water (20 ml) were added with stirring. The layers were separated, and the aqueous phase was extracted with ether. The combined organic phase was dried ($Na_2SO_4$), filtered, and evaporated to give 85 mg (37%) of the desired product.

Following the procedure of Example 2, but replacing the amine hydrochloride and N-methylmorpholine with the above resultant product, gave the desired major diastereomer in 35% yield after chromatography. FAB mass spectrum: $(M+K)^+ = 570$.

Anal. calcd. for $C_{30}H_{49}N_3O_5$: C, 67.8; H, 9.3; N, 7.9. Found: C, 67.7; H, 9.6; N, 7.3.

EXAMPLE 8

Boc-Phe-Ala Amide of (3S)-Amino-2-hydroxy-2-isopentyl-5-methylhexanal

Following the procedure of example 3 with the resultant compound of Example 7, gave the desired compound.

EXAMPLE 9

Boc-Phe-Ala Amide of
(4S)-Amino-2,8-dimethyl-5hydroxy-5-vinylnonane

Scale up of the procedure of Example 6 led to the isolation of the minor diastereomer pure after chromatography. Treatment as in Example 7 provided the desired isomer of the resultant product of Example 7.

EXAMPLE 10

Boc-Phe-Ala Amide of
(3S)-Amino-2-hydroxy-2-isopentyl-5-methylhexanal

Following the procedure of Example 3 with the resultant compound of Example 9, gave the desired isomer of the resultant product of Example 8.

EXAMPLE 11

(2S)-t-Butyloxycarbonylamino-1-cyclohexylbut-3-ene

A 0° C. solution of potassium hexamethyldisilazide (22.9 mmol in 115 ml of 5:1, THF:dimethyl sulfoxide (DMSO) was added dropwise to triphenylmethyl-phosphonium iodide (24.8 mmol). After stirring at 0° C. for 1 hour, the solution was cooled to −78° C. and a solution of Boc-cyclohexylalaninal [4.90 g, 19.08 mmol, prepared by Swern oxidation (Mancuso, A. J.; Huang, S.-L.; and Swern, D. *J. Org. Chem.* 1978, 43, 2480) of Boc-cyclohexylalaninol] in dry THF (95 ml) was added. After stirring at −78° C. for 1 hour, the mixture was allowed to warm to room temperature. The reaction mixture was quenched with aqueous ammonium chloride and extracted with ether (2×300 ml). The combined organic phase was washed with 10% HCl (200 ml), saturated $NaHSO_3$ (2×200 ml), $H_2O$ (2×200 ml), saturated $NaHCO_3$ (2×200 ml), and brine (200 ml), dried ($MgSO_4$), filtered, and evaporated. The residue was purified by chromatography (40M $SiO_2$; ether:hexane, 15:85) to give the desired compound in 60% yield. Mass spectrum: $(M+H)^+=254$.

EXAMPLE 12

(2RS,3S)-3-t-Butyloxycarbonylamino-4-cyclohexyl-1,2-oxobutane

To a stirred solution of the resultant compound of Example 11 (0.51 g, 2.0 mmol) in dichloromethane (20 ml) was added 3-chloroperoxybenzoic acid (1.51 g of 80%, 7.0 mmol). After 60 hours, the mixture was cooled to 0° C., and 0° C. 10% $Na_2SO_3$ (5 ml) was added with stirring. The solid was filtered off and extracted with dichloromethane. The combined organic phase was diluted with ether and washed sequentially with 0° C. 10% $Na_2SO_3$ (6 ml), saturated $NaHCO_3$ (2×6 ml), and water (5 ml). Drying ($MgSO_4$), filtering, and evaporating provided the desired material (329 mg, 61%) after chromatography. Analysis of the NMR spectrum revealed an 8:1 mixture of 2R:2S diastereomers. Mass spectrum: $(M+H)^+=270$.

EXAMPLE 13

(2RS,3S)-3-Amino-1-chloro-4-cyclohexyl-2-hydroxybutane Hydrochloride

To a stirred solution of the resultant product of Example 12 (110 mg, 0.408 mmol) in anhydrous methanol (5 ml) was added anhydrous methanol saturated with anhydrous HCl (10 ml). The solvent was evaporated after 14 hours, and the residue was chased several times with ether and dichloromethane in order to obtain 100 mg (100%) of the desired product as a crystalline solid which was used without further purification.

EXAMPLE 14

Boc-Phe-Ala Amide of
(2R,3S)-3-Amino-1-chloro-4-cyclohexyl-2-hydroxybutane

The resultant compound of Example 13 was coupled with Boc-Phe-Ala according to the procedure of Example 2 to give the desired product after chromatography. Mass spectrum: $M^+=523$.

Anal. calcd. for $C_{27}H_{42}N_3O_5Cl$: C, 61.9; H, 8.1., N, 8.0. Found: C, 62.0; H, 8.2; N, 7.7.

EXAMPLE 15

(2RS,3S)-3-Amino-1-bromo-4-cyclohexyl-2-hydroxybutane Hydrobromide

To a stirred solution of the resultant product of Example 12 (110 mg, 0.408 mmol) in dichloromethane (5 ml) was added HBr/acetic acid (30–32%, 1.0 ml). The solvent was evaporated after 1 hour, and the residue was chased several times with toluene. Drying under high vacuum yielded 135 mg (0.100%) of the desired product as a crystalline solid which was used without further purification.

EXAMPLE 16

Boc-Phe-Ala Amide of
(2R,3S)-3-Amino-1-bromo-4-cyclohexyl-2-hydroxybutane

The resultant compound of Example 15 was coupled to Boc-Phe-Ala according to the procedure of Example 2 to give the desired product (180 mg, 78%) after recrystallization from ethyl acetate/hexane. Mass spectrum: $M^+=567$.

Anal. calcd. for $C_{27}H_{42}N_3O_5Br$: C, 57.0; H, 7.4; N, 7.3. Found: C, 56.6; H, 7.5; N, 6.9.

EXAMPLE 17

(2S)-t-Butyloxycarbonylamino-1-cyclohexyl-6-methyl-hept-3-ene

To a stirred −78° C. solution of Boc-cyclohexylalanine methyl ester (40 g, 140 mmol) in anhydrous toluene (250 ml) was added diisobutylaluminum hydride (130M %, 1.5M solution in toluene, 121.4 ml) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 ml/200 ml) under dry $N_2$ was added 1,1,1,3,3,3-hexamethyldisilazane (209M %, 49.07 g) dropwise. After stirring at 0° C. for 1 hour, the resulting solution was added via cannula to a 0° C. flask containing isopentyltriphenylphosphonium bromide (209M %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 ml) followed by aqueous Rochelle salts (100 ml saturated solution and 500 ml $H_2O$). The mixture was then extracted with ethyl acetate (2x). The combined extracts were washed with water and brine. Drying (MgSO₄) and evaporating provided crude alkene which was chromatographed on silica gel (ether/hexane) to give 16.5 g (38%) of the desired compound as an 85:15 mixture of cis:trans isomers. Mp=53°-55° C. Mass spectrum: M+=309.

Anal. calcd. for $C_{19}H_{35}NO_2$: C, 73.7; H, 11.4; N, 4.5. Found: C, 73.8; H, 11.4; N, 4.5.

EXAMPLE 18

(2S)-t-Butyloxycarbonylamino-1-cyclohexyl-3-hydroxy-6-methylheptan-4-one

To a solution of the resultant compound of Example 17 (8.50, 27.5 mmol) in dry THF (150 ml) were added OsO₄ (2.8 ml of a 2.5% solution in t-butanol and N-methylmorpholine N-oxide (9.28 g, 68.7 mmol). After 4d the mixture was partitioned between ether (200 ml) and brine (100 ml). The aqueous layer was back-extracted with ether (2×100 ml), and the combined organic phase was washed with 10% Na₂SO₃, 0.1M H₃PO₄, and brine. Drying (MgSO₄) and evaporating provided a residue (10.81 g) which was chromatographed on silica gel to remove the four diastereomeric diols from 0.70 g (7%) of the desired product. Mass spectrum: (M+H)=342.

EXAMPLE 19

Boc-Phe-His Amide of (2S)-Amino-1-cyclohexyl-3-hydroxy-6-methylheptan-4-one

The resultant product of Example 18 (220 mg, 0.645 mmol) was treated with 4M HCl/dioxane for 6 hours. Evaporation and drying under high vacuum provided the corresponding amine hydrochloride which was dissolved in dry dimethylformamide (DMF, 1.0 ml), treated with Boc-Phe-His (260 mg), N-methylmorpholine (0.142 ml), and 1-hydroxybenzotriazole hydrate (261 mg), cooled to −23° C., and then treated with 1-ethyl-3-(dimethylaminopropyl)carbodiimide hydrochloride (124 mg). Evaporation after 16 hours provided a thick oil which was partitioned between ethyl acetate (60 ml) and saturated NaHCO₃ (30 ml). The organic phase was washed with brine, dried (MgSO₄), and evaporated to give a residue which was chromatographed on silica gel (dichloromethane/methanol) to give 161 mg (40%) of the desired product. Mass spectrum: (M+H)+=626.

Anal. calcd. for $C_{34}H_{51}N_5O_6$: C, 65.3; H, 8.3; N, 11.2. Found: C, 65.6; H, 8.3., N, 11.2.

The compounds of the present invention can be used in the form of salts derived from inorganic or organic acids. These salts include but are not limited to the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the molar concentration required to cause 50% inhibition, expressed as the IC₅₀, is calculated. When tested in accordance with the foregoing procedure, the compounds of the invention demonstrated IC₅₀'s in the range of $10^{-5}$ to $10^{-9}$M as seen in Table I.

TABLE I

| Example Number | IC₅₀ (nM) |
|---|---|
| 3 | 10 |
| 14 | 400 |
| 16 | 700 |
| 19 | 10 |

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparation, for example, sterile injectable aqueous or oleagenous suspensions may be formulated according to the known art using suitable dispersion or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A renin inhibiting compound of the formula:

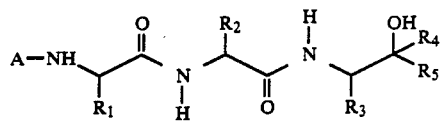

wherein A is an N-protecting group; $R_1$ is selected from arylalkyl and substituted arylalkyl wherein the substituent is loweralkyl, loweralkoxy or halo; $R_2$ is selected from loweralkyl and imidazoylmethyl; and $R_3$ is selected from loweralkyl and cycloalkylalkyl; and $R_4$ is —CHO, halomethyl or alkanoyl; and $R_5$ is hydrogen or loweralkyl and pharmaceutically acceptable salts thereof.

2. The renin inhibiting compound of claim 1 wherein $R_1$ is benzyl; $R_2$ is methyl or (4-imidazoyl)methyl; and $R_3$ is isobutyl or cyclohexylmethyl.

3. The renin inhibiting compound of claim 2 wherein A is Boc; $R_4$ is chloromethyl; and $R_5$ is hydrogen.

4. The renin inhibiting compound of claim 2 wherein A is Boc; $R_4$ is isopentanoyl; and $R_5$ is hydrogen.

5. A pharmaceutical composition for treating renin-associated hypertension, comprising a pharmaceutical carrier and a therapeutically effective amount of the compound of claim 1.

6. A method of treating hypertension comprising administering to a host in need of such treatment a therapeutically effective amount of a compound of claim 1.

* * * * *